United States Patent
Miller et al.

(10) Patent No.: US 11,135,573 B2
(45) Date of Patent: Oct. 5, 2021

(54) PHOSPHATE-PROMOTED NICKEL CATALYST FOR HIGH TEMPERATURE OLIGOMERIZATION

(71) Applicant: PURDUE RESEARCH FOUNDATION, West Lafayette, IN (US)

(72) Inventors: Jeffrey T. Miller, West Lafayette, IN (US); Guanghui Zhang, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 92 days.

(21) Appl. No.: 16/361,411

(22) Filed: Mar. 22, 2019

(65) Prior Publication Data
US 2020/0298215 A1      Sep. 24, 2020

(51) Int. Cl.
| | | |
|---|---|---|
| *B01J 27/185* | (2006.01) | |
| *B01J 35/10* | (2006.01) | |
| *C07C 2/24* | (2006.01) | |

(52) U.S. Cl.
CPC ....... *B01J 27/1853* (2013.01); *B01J 35/1019* (2013.01); *B01J 35/1023* (2013.01); *B01J 35/1061* (2013.01); *C07C 2/24* (2013.01); *B01J 2523/847* (2013.01); *C07C 2527/185* (2013.01)

(58) Field of Classification Search
CPC ........ B01J 27/18; B01J 27/1853; B01J 21/08; B01J 21/04; B01J 21/12; B01J 37/04; B01J 37/08; B01J 2231/20

USPC ................................................. 502/208, 213
See application file for complete search history.

(56) References Cited

U.S. PATENT DOCUMENTS

| | | | | |
|---|---|---|---|---|
| 2,542,813 | A | * | 2/1951 | Heath ................. B01J 27/1853 423/306 |
| 2,888,501 | A | * | 5/1959 | Carr ...................... C07C 5/2791 585/740 |
| 2,969,408 | A | * | 1/1961 | Nowlin ..................... C07C 2/36 585/513 |
| 3,297,778 | A | * | 1/1967 | Noddings ............... C07C 11/02 585/667 |
| 3,352,931 | A | * | 11/1967 | Zuech ..................... B01J 31/14 585/369 |
| 3,501,549 | A | * | 3/1970 | Gates ........................ C07C 5/48 585/618 |
| 3,538,019 | A | * | 11/1970 | Wright ................ B01J 27/1853 502/184 |
| 4,044,066 | A | * | 8/1977 | Ripley ................ B01J 27/1853 585/622 |
| 4,361,705 | A | * | 11/1982 | Marcelin .................. B01J 27/16 568/462 |
| 4,680,105 | A | * | 7/1987 | Coombs ................ B01J 23/755 208/251 H |
| 2014/0274673 | A1 | * | 9/2014 | Kauffman ............ B01J 27/1856 502/213 |
| 2020/0298216 | A1 | * | 9/2020 | Miller .................... B01J 37/088 |

\* cited by examiner

*Primary Examiner* — Patricia L. Hailey
(74) *Attorney, Agent, or Firm* — Edmonds & Cmaidalka, P.C.

(57) ABSTRACT

An oligomerization catalyst, oligomer products, methods for making and using same. The catalyst can include a supported nickel phosphate compound. The catalyst is stable at oligomerization temperatures of 500° C. or higher and particularly useful for making oligomer products containing C4 to C26 olefins having a boiling point in the range of 170° C. to 360° C.

6 Claims, 4 Drawing Sheets

PHOSPHATE-PROMOTED NICKEL CATALYST FOR HIGH TEMPERATURE OLIGOMERIZATION

GOVERNMENT LICENSE RIGHTS

This invention was made with government support under Cooperative Agreement No. EEC-1647722 awarded by the National Science Foundation. The government has certain rights in the invention.

BACKGROUND

Field of the Invention

Embodiments of the present invention generally relate to light hydrocarbon alkene oligomerization. More particularly, embodiments relate to new catalyst for light hydrocarbon alkene oligomerization.

Description of the Related Art

Oligomerization is a process by which short chain olefin monomers are converted to intermediate chain-length olefins having relatively fewer monomers as compared to polymerization where the number of monomers in the chain is high resulting in high molecular weight products, polymers. Such conversion of shorter chain olefins (formed from steam cracking, Fluid Catalytic Cracking, Fischer-Tropsch processes, etc.) to longer chain hydrocarbons has been of considerable interest in the past. Gasoline/motor fuel, for example, has been produced by the oligomerization of olefins in cracked refinery gas since the early 1930's. The petrochemical industry also utilizes ethylene oligomerization for production of linear higher carbon α-olefins to be used for detergents, plasticizers, and a variety of industrial chemicals.

Conventional processes for ethylene oligomerization utilizing homogeneous catalysts have been based on nickel (Ni), titanium (Ti), zirconium (Zr), and chromium (Cr) complexes. These homogeneous catalysts show high activity, good control of chain length and preferential formation of linear alpha olefins. One example of such process for converting ethylene to high carbon olefins is the Shell Higher Olefins Process (SHOP) that was developed by Wilhelm Keim. The SHOP is catalyzed by a Ni complex bearing a chelating ligand with a neutral phosphine and an anionic oxygen donor. Another example is a titanium chloride catalyst in combination with aluminum ethyl chloride $Al(C_2H_5)_2Cl$ that was discovered by Karl Ziegler and Heinz Martin and used to catalyze the conversion of ethylene to 1-butene with high selectivity. This has been commonly known as the Ziegler catalyst.

Various modifications of the Ziegler catalyst have been developed over the years. Chauvin et al., for example, developed the Alphabutol process for 1-butene production from ethylene with a titanium catalyst, which can achieve a Turnover Frequency (TOF) approaching 106 $h^{-1}$. Zirconium alkoxides display a lower activity but a comparable selectivity for converting ethylene to 1-butene. The Chevron Phillips (Gulfene) and Ineos (Ethlyl) processes used an aluminum Zeigler catalyst for converting ethylene to 1-butene. Idemitsu Kosan Co. Ltd. developed zirconium (IV) complex for oligomerization. IFP Energies nouvelles (IFPEN) and SABIC-Linde used a zirconium precursor, a ligand, and an aluminum co-catalyst. Phillip's used a trimerization catalyst where the active metal is chromium (Cr) on an amorphous support of porous silica.

After the success of nickel, titanium, zirconium and chromium, other transition metal complexes of cobalt and iron were explored as potential catalysts for olefin oligomerization. The Brookhart group and Britovsek et al., for example, studied iron (II) and cobalt (II) catalysts bearing pyridine ligands. Such catalysts, however, were sensitive to impurities in the feed, sensitive to temperature, difficult to separate from the products, and/or had low potential for reusability.

There is a need, therefore, for a new and improved oligomerization catalyst capable of oligomerization at acceptable conversion rates and overcoming the aforementioned shortcomings of predecessor catalysts for oligomerization.

SUMMARY

An oligomerization catalyst, oligomer products and methods for making and using the same are provided. The catalyst can include a supported nickel phosphate compound and is stable at oligomerization temperatures of 500° C. or higher. The catalyst is particularly useful for making oligomers containing C4 to C26 olefins having a boiling point in the range of 170° C. to 360° C., which can be used to produce diesel and jet fuels.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
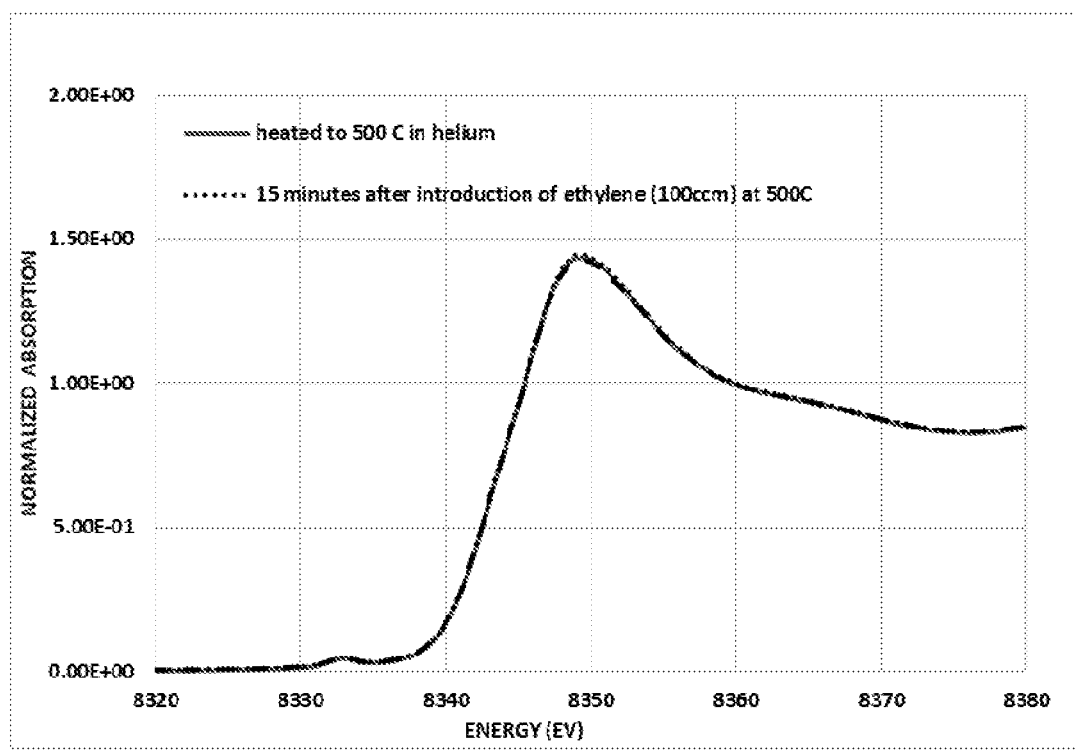
FIG. 1 shows a XANES spectra of an inventive Ni—P/$SiO_2$ catalyst provided in the Example below.

Certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function. Furthermore, in the following discussion and in the claims, the terms "including" and "comprising" are used in an open-ended fashion, and thus should be interpreted to mean "including, but not limited to."

All numerical values in this disclosure can be exact or approximate values ("about") unless otherwise specifically stated. Accordingly, various embodiments of the disclosure can deviate from the numbers, values, and ranges disclosed herein without departing from the intended scope.

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise.

The phrase "consisting essentially of" means that the described/claimed composition does not include any other components that will materially alter its properties by any more than 5% of that property, and in any case, does not include any other component to a level greater than 3 wt %.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

A nickel-based catalyst useful for olefin oligomerization that retains stability at high temperature is provided. It has been surprisingly an unexpectedly discovered that oligomerization can be achieved at high reaction temperatures using a nickel-based catalyst having a phosphate ligand. With the presence of a phosphate ligand bonded to the nickel metal center, the nickel surprisingly and unexpectedly remained in the +2 oxidation state at reaction temperatures at or above 500° C., and exhibited high stability and activity for light hydrocarbon oligomerization. Not wishing to be bound by theory, it is believed that the presence of a phosphate ligand on the nickel metal complex prevents or severely inhibits the reduction of Ni(II) to Ni(0) at reaction temperatures at or above 500° C., allowing the oligomerization of light hydrocarbons to higher molecular weight oligomers at much higher temperatures than could be achieved before.

By "oligomer(s)", it is meant dimers, trimers, tetramers, and other molecular complexes having less than 26 repeating units. Oligomers provided herein are typically gases or liquids at ambient temperature, and can include low melting solids, including waxes, at ambient temperature. In some embodiments, the oligomers provided herein can have an atomic weight or molecular weight of less than 10,000 AMU (Da), such as about 5,000 or less, 1,000 or less, 500 or less, 400 or less, 300 or less, or 200 or less. The molecular weight of the oligomer, for example, can range from a low of about 50, 250 or 350 to a high of about 500, 3,000, 7,000, or 9,000 AMU (Da).

The nickel-based catalyst does not require a co-catalyst or activator to create a vacant coordination site that will coordinate, insert, and oligomerize the olefin(s). For the purposes of this specification, the terms "cocatalyst" and "activator" are used herein interchangeably and refer to any compound, other than the reacting olefin, that can activate the nickel-based catalyst by converting the neutral catalyst compound to a catalytically active catalyst compound cation. For example, the following co-catalyst and/or activators are not required: alumoxanes, aluminum alkyls, ionizing activators, which may be neutral or ionic, alumoxane compounds, modified alumoxane compounds, and ionizing anion precursor compounds that abstract one reactive, σ-bound, metal ligand making the metal complex cationic and providing a charge-balancing noncoordinating or weakly coordinating anion.

The nickel-based catalyst can be deposited on, contacted with, bonded to, or incorporated within, adsorbed or absorbed in, or on, one or more supports or carriers. The support material can be any suitable support material. For example, the support material can be a porous support material, such as inorganic oxides. Other support materials can include silica, which may or may not be dehydrated, fumed silica, alumina, silica-alumina or mixtures thereof. Other supports include magnesia, titania, zirconia, montmorillonite, phyllosilicate, zeolites, clays and the like. Other support materials can include nanocomposites, and aerogels. Combinations of these support materials can be used, for example, silica-chromium, silica-alumina, silica-titania and the like.

Particular, non-limiting examples of more preferred catalyst supports include: silicon dioxide, aluminum oxide, titanium dioxide, zeolites, silica-alumina, cerium dioxide, zirconium dioxide, magnesium oxide, silica pillared clays, metal modified silica, metal oxide modified silica, metal oxide modified silica-pillared clays, silica-pillared micas, metal oxide modified silica-pillared micas, silica-pillared tetrasilicic mica, silica-pillared tainiolite, and combinations thereof. Such supports are commercially available or prepared by techniques known to those skilled in the catalysis art.

The support material can have a surface area in the range of from about 10 $m^2/g$ to about 700 $m^2/g$, a pore volume in the range of from about 0.1 cc/g to about 4.0 cc/g and an average particle size in the range of from about 5 μm to about 500 μm. More preferably, the support material can have a surface area in the range of from about 50 $m^2/g$ to about 500 $m^2/g$, pore volume of from about 0.5 cc/g to about 3.5 cc/g and average particle size of from about 10 μm to about 200 μm. The surface area can range from a low of about 50 $m^2/g$, 150 $m^2/g$, or 300 $m^2/g$ to a high of about 500 $m^2/g$, 700 $m^2/g$, or 900 $m^2/g$. The surface area also can range from a low of about 200 $m^2/g$, 300 $m^2/g$, or 400 $m^2/g$ to a high of about 600 $m^2/g$, 800 $m^2/g$, or 1,000 $m^2/g$. The average pore size of the support material can range of from about 10 Å to 1000 Å, about 50 Å to about 500 Å, about 75 Å to about 350 Å, about 50 Å to about 300 Å, or about 75 Å to about 120 Å.

In another embodiment the support material can be one or more types of support materials which may or may not be treated differently. For example, one could use two different silicas each having different pore volumes or calcined at different temperatures. Likewise, one could use a silica that had been treated with a scavenger or other additive and a silica that had not.

The nickel-based catalyst can convert light hydrocarbon alkenes to higher molecular weight oligomers at high temperatures and suitable oligomerization pressures. The light hydrocarbons or hydrocarbon feed stream can be or can include natural gas, natural gas liquids, or mixtures of both. The hydrocarbon feed stream can be derived directly from shale gas or other formations. The hydrocarbon feed stream can also originate from a refinery, such as from a FCC, coker, steam cracker, and pyrolysis gasoline (pygas) as well as alkane dehydrogenation processes, for example, ethane, propane and butane dehydrogenation. The hydrocarbon feed stream can also be or can include syngas and coal gas.

The hydrocarbon feed stream can be or can include one or more olefins having from about 2 to about 12 carbon atoms. The hydrocarbon feed stream can be or can include one or more linear alpha olefins, such as ethene, propene, butenes, pentenes and/or hexenes. The process is especially applicable to ethene and propene oligomerization for making C4 to about C26 oligomers.

The hydrocarbon feed stream can contain greater than about 65 wt % olefins, such as greater than about 70 wt. % olefins or greater than about 75 wt % olefins. For example, the hydrocarbon feed stream can contain one or more C2 to C12 olefins in amounts ranging from a low of about 50 wt %, 60 wt % or 65 wt % to a high of about 70 wt %, 85 wt % or 100 wt %, based on the total weight of the feed stream. The hydrocarbon feed stream also can include up to 80 mol % alkanes, for example, methane, ethane, propane, butane, and pentane; although the alkane generally comprises less than about 50 mol % of the hydrocarbon feed stream, and preferably less than about 20 mol % of the hydrocarbon stream.

The hydrocarbon feed can have a temperature of 250° C. or higher. For example, the temperature of the hydrocarbon feed can range from a low of about 250°, 450° C., or 500° to a high of about 550° C., 600° C., or 700° C. The temperature of the hydrocarbon feed also can be 420° C. or higher, 450° C. or higher, 480° C. or higher, 500° C. or higher, 525° C. or higher, 550° C. or higher, 560° C. or higher, 570° C. or higher, or 575° C. or higher, or 600° C. or higher.

The resulting oligomer(s) can be or can include one or more olefins having from 4 to 26 carbon atoms, such as 12 to 20 carbon atoms, or 16 to 20 carbon atoms. The resulting oligomers, for example, can include butene, hexene, octene, decene, dodecene, tetradecane, hexadecane, octadecene and eicosene and higher olefins, as well as any combinations thereof. The resulting oligomer(s) also can have less than about 5% aromatics and less than about 10 ppm sulfur. The resulting oligomer(s) also can have zero or substantially no aromatics and zero or substantially no sulfur.

The resulting oligomer(s) are useful as precursors, feedstocks, monomers and/or comonomers for various commercial and industrial uses including polymers, plastics, rubbers, elastomers, as well as chemicals. For example, these resulting oligomer(s) are also useful for making polybutene-1, polyethylene, polypropylene, polyalpha olefins, block copolymers, detergents, alcohols, surfactants, oilfield chemicals, solvents, lubricants, plasticizers, alkyl amines, alkyl succinic anhydrides, waxes, and many other specialty chemicals.

The resulting oligomer(s) are especially useful for production of diesel and jet fuels, or as a fuel additive. In certain embodiments, the resulting oligomer(s) can have a boiling point in the range of 170° C. to 360° C. and more particularly 200° C. to 300° C. The resulting oligomer(s) also can have a Cetane Index (CI) of 40 to 100 and more particularly 65 to 100. The resulting oligomer(s) also can have a pour point of −50° C. or −40° C.

As mentioned above, it has been surprisingly an unexpectedly discovered that the nickel-based catalyst described herein can oligomerize light alkene hydrocarbons to higher molecular weight oligomers at reaction temperatures never thought possible. Suitable reaction temperatures can exceed 500° C., such as about 525° C., 550° C., and 600° C. The reaction temperature, for example, can range from about 500° C. to about 600° C. or higher. Of course, lower reaction temperatures are also possible, such as between about 135° C., 200° C. or 225° C. and about 350° C., 400° C., or 500° C. Another significant advantage is that conventional oligomerization pressures can be used. For example, the reaction pressure can range from about 400 psig to about 4000 psig (27.5 Bar to 276 Bar), or about 500 psig to about 1500 psig (34.5 Bar to 103 Bar). The reaction pressure can also range from a low of about 400 psig (27.5 Bar), 500 psig (34.5 Bar) or 600 psig (41.4 Bar) to a high of about 1,000 psig (68.9 Bar), 1,200 psig (82.7 Bar), or 2,000 psig (138 Bar).

The oligomerization process can be carried out using any conventional technique. The process can be carried out, for example, in a continuous stirred tank reactor, batch reactor or plug flow reactor. One or more reactors operated in series or parallel can be used. The process can be operated at partial conversion to control the molecular weight of the product and unconverted olefins can be recycled for higher yields. Further, once the catalyst is deactivated with high molecular weight carbon, or coke, it can be regenerated using known techniques in the art, including for example, by combustion in air at a temperature of about 400° C. or higher.

EXAMPLES

The foregoing discussion can be further described with reference to the following non-limiting examples, which compare the stability and effectiveness of an inventive nickel-phosphate catalyst to a convention nickel oxide supported catalyst.

The comparative Ni/SiO$_2$ (nickel on silica) catalyst was prepared by dissolving 15.00 g of Ni (NO$_3$)$_2$.6H$_2$O (nickel nitrate hexahydrate) in 100 mL of deionized (DI) water followed by the addition of 25.0 mL of concentrated NH$_4$OH (ammonium hydroxide). A clear blue solution was obtained with a pH of 11. Then 50.0 g of SiO$_2$ (Davisil Grade 636, pore size 60 Å, 35-60 mesh, surface area 480 m$^2$/g) was added to the solution and the obtained suspension was stirred at room temperature for 20 mins. An additional 5.0 mL of NH$_4$OH was added to maintain the pH at 11 at the end of the reaction. It was stirred at room temperature for an additional 10 mins before filtration and thorough washing with DI water. The obtained nickel (Ni)-adsorbed SiO$_2$ was dried at 125° C. overnight and calcined at 300° C. for 30 mins (5° C. per minute ramp to 300° C.). The Ni loading as determined by Atomic Adsorption Spectroscopy (AAS) was 2.7 wt %.

The inventive Ni—P/SiO$_2$ (nickel phosphate on silica) catalyst was prepared by diluting 0.4174 g of H$_3$PO$_4$ (phosphoric acid) (85% aq.) with 3.5 mL of de-ionized (DI) water. This solution was then impregnated with 5.0 g of the Ni/SiO$_2$ that was prepared as described above. The impregnated solution was calcinated in air at 600° C. (5° C. per minute ramp to 600° C.) for 1 hour and the Ni—P/SiO$_2$ was obtained (Scheme 1). The Ni loading as determined by AAS was 2.6 wt %.

Scheme 1: Synthesis of SiO$_2$-supported Ni(II) catalyst.

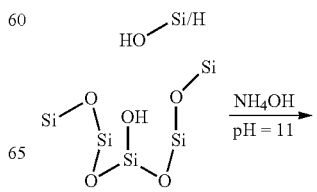

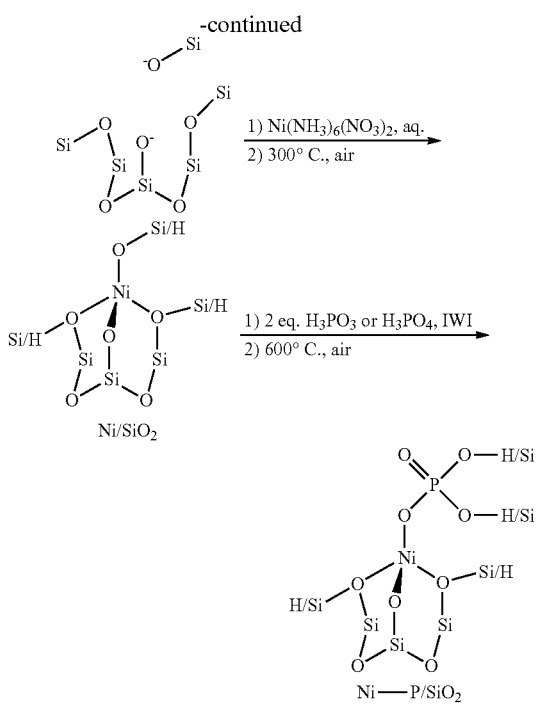

The ethylene oligomerization catalytic performance testing was conducted in a vertical, 10.5 mm ID quartz tube reactor equipped with mass flow controllers. The catalyst was supported on quartz wool with an internal thermocouple monitoring the temperature of the catalyst bed. The oligomerization products were products being monitored by a HP6890 series Gas Chromatograph (GC) system with Agilent J&W HP-1 GC Column.

Example 1

The Ni—P/SiO$_2$ catalyst was purged with ultra-high purity nitrogen to remove any adsorbed moisture. It was then heated to a range of temperatures from 200 to 580° C. to see if it was active at any of these temperatures, by introducing ethylene into the reactor and monitoring products through the GC system. A sample of Ni—P/SiO$_2$ catalyst (0.1 g catalyst, 0.9 g silica) and 5% ethylene (balance nitrogen) at a flow rate of 25 ccm (cubic centimeter per minute) was used at atmospheric pressure for these tests. Oligomerization products started to appear at temperatures above 500° C.

Example 2

A fresh sample of catalyst (0.2 g catalyst, 0.8 g silica) was loaded into the reactor and heated to 500° C. Then 25 ccm of 5% ethylene was introduced into the reactor at atmospheric pressure. Products were monitored at 12-minute intervals through the GC system.

Example 3

A fresh sample of the same catalyst was heated in nitrogen to 500° C. and then pretreated with 99% hydrogen at this temperature for 30 minutes. Ethylene was introduced into the reactor and the products monitored through the GC system.

Example 4

A fresh sample of the same catalyst was heated to 500° C. in nitrogen and 25 ccm of 5% ethylene and 5 ccm of 99% hydrogen were co-fed into the reactor. The same series of tests were repeated at 550° C. with one difference, the catalyst loading was 0.5 g catalyst and 0.5 g silica (Table I). To compare with the Ni—P/SiO$_2$ catalyst, the same series of tests as above were performed for the Ni/SiO$_2$ (0.5 g) catalyst. No catalytic activity/products were observed at any of these conditions. The Ni/SiO$_2$ catalyst was not active at these elevated temperatures.

TABLE 1

OLIGOMERIZATION TESTS ON Ni—P/SiO$_2$

| Catalyst loading | Temperature (° C.) | Pressure (atm) | Ethylene Flow (ccm) | Hydrogen (99%) flow (ccm) | Conversion (%) | Selectivity for Butene (%) |
|---|---|---|---|---|---|---|
| EXAMPLE 2: Reaction in 5% Ethylene in Nitrogen | | | | | | |
| Ni—P/SiO$_2$ (0.2 g) | 500 | 1 | 25 | — | 0.28 | 100 |
| Ni—P/SiO$_2$ (0.5 g) | 550 | 1 | 25 | — | 0.63 | 80 |
| EXAMPLE 3: Reaction in 5% Ethylene in Nitrogen and co-feeding with 99% Hydrogen | | | | | | |
| Ni—P/SiO$_2$ (0.2 g) | 500 | 1 | 25 | 5 | 0.15 | 100 |
| Ni—P/SiO$_2$ (0.5 g) | 550 | 1 | 25 | 5 | 0.4 | 78 |
| EXAMPLE 4: Reaction in 5% Ethylene in Nitrogen after pretreatment with 99% Hydrogen for 30 minutes | | | | | | |
| Ni—P/SiO$_2$ (0.2 g) | 500 | 1 | 25 | — | 0.13 | 100 |
| Ni—P/SiO$_2$ (0.5 g) | 550 | 1 | 25 | — | 0.35 | 79 |

The presence of hydrogen co-feed decreased the conversion of the Ni—P/SiO$_2$ due to reduction in partial pressure of ethylene. The Ni—P/SiO$_2$ catalyst was tested at 550° C. in ethylene for 6 hours without any deactivation. Only even carbon numbered components, up to hexenes, were detected in which butenes were the main products. The active nickel sites mainly dimerized ethene to butene while only a limited amount of butene further reacted toward hexene. The selectivity towards butene, and hexene amounted to 80%, and 20% respectively.

The Ni—P/SiO$_2$ and the Ni/SiO$_2$ catalysts were examined on the advanced photon source (APS) beamline facility at Argonne national lab (ANL). Spectroscopic data collection for Extended X-ray Absorption Fine Structure (EXAFS) and X-ray Absorption Near-Edge Structure (XANES) was carried out at ambient and reaction conditions of (500° C. and 550° C.) with and without the presence of hydrogen. Catalyst samples (~10 mg) were pressed into a cylindrical sample holder consisting of six wells, forming a self-supporting wafer to prepare for this test.

It was observed in the in-situ XANES (FIG. 1) for the Ni—P/SiO$_2$ catalyst that under reaction conditions, after introduction of ethylene for fifteen minutes, the Ni(II) was stable at 500° C. and even after co-feeding with hydrogen for fifteen minutes at 550° C., the Ni (II) showed no signs of reduction. The spectra are indistinguishable from each other, which implies stable tetrahedral geometry of Ni(II) and +2 oxidation state of Ni under reaction conditions.

Figure 2:
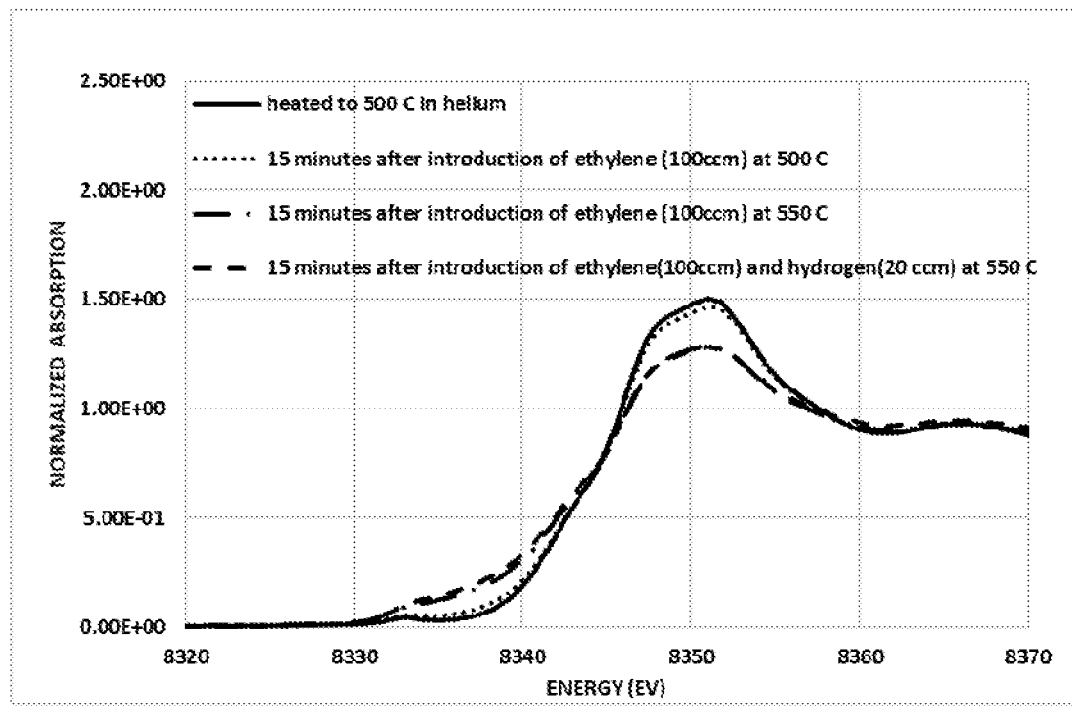
FIG. 2 shows a XANES spectra of a comparative Ni/$SiO_2$ catalyst provided in the Example below.

It can also be seen from the XANES for Ni/SiO$_2$ (FIG. 2), there was a slight change in edge peak height at 500° C. in presence of ethylene and at 550° C. a bigger change was observed. The change in edge peak height signifies a decrease in the number of Ni (II) atoms. The pre-edge almost disappears at 550° C. indicating loss of tetrahedral coordinated Ni (II) and reduction to Ni (0). The leading edge energy of the XANES after reaction (8333.0 eV) is identical to that of metallic Ni foil, indicating the reduction of Ni (II) to metallic Ni nanoparticles.

The XANES data were fit to find the fraction of each oxidation state of nickel in both catalyst samples at ambient and reaction conditions. Ni foil was taken as reference for the Ni (0) to determine the percentage of reduced Ni in both catalyst samples as calculated in the Table II.

TABLE II

XANES DATA

| Sample | Treatment | Edge energy (eV) | Pre-edge energy (eV) | Oxidation state |
|---|---|---|---|---|
| Ni—P/SiO$_2$ | 500° C., air Measured at 550° C. | 8342.8 | 8333.0 | Ni(II) |
| | 500° C., H$_2$ + C$_2$H$_4$ Measured at 550° C. | 8342.8 | 8333.0 | Ni(II) |
| | 500° C., C$_2$H$_4$ Measured at 550° C. | 8342.8 | 8333.0 | Ni(II) |
| Ni/SiO$_2$ | 500° C., air Measured at 550° C. | 8342.2 | 8333.0 | Ni(II) |
| | 500° C., C$_2$H$_4$ Measured at 550° C. | 8342.2 (pre-edge) | 8333.0 | 5.9% Ni(0) + 94.1% Ni(II) |
| | 550° C., C$_2$H$_4$ Measured at 550° C. | 8333.0 | — | 34.1% Ni(0) + 65.9% Ni(II) |
| | 550° C., C$_2$H$_4$ + H$_2$ Measured at 550° C. | 8333.0 | — | 63.9% Ni(II) + 36.1% Ni(0) |
| Ni foil | RT | 8333.0 | — | Ni(0) |

Figure 3:
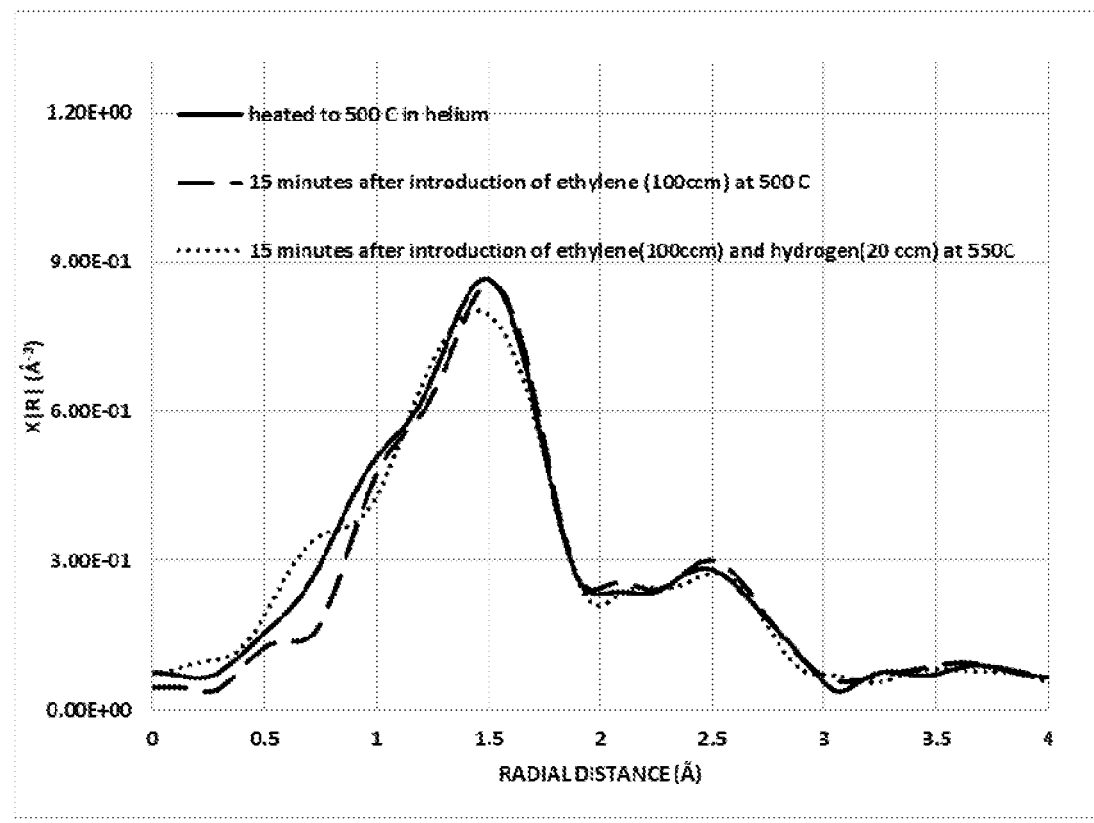
FIG. 3 shows an EXAFS spectra of the inventive Ni—P/$SiO_2$ catalyst provided in the Example below.

The EXAFS spectra was useful in determining the distances between Ni and the neighboring atoms, as well as the coordination number and the composition of the surrounding atoms. As can be seen in FIG. 3, the peaks were almost similar for Ni—P/SiO$_2$ EXAFS at all conditions. The slight changes in the EXAFS spectra are due to the background noise.

Figure 4:
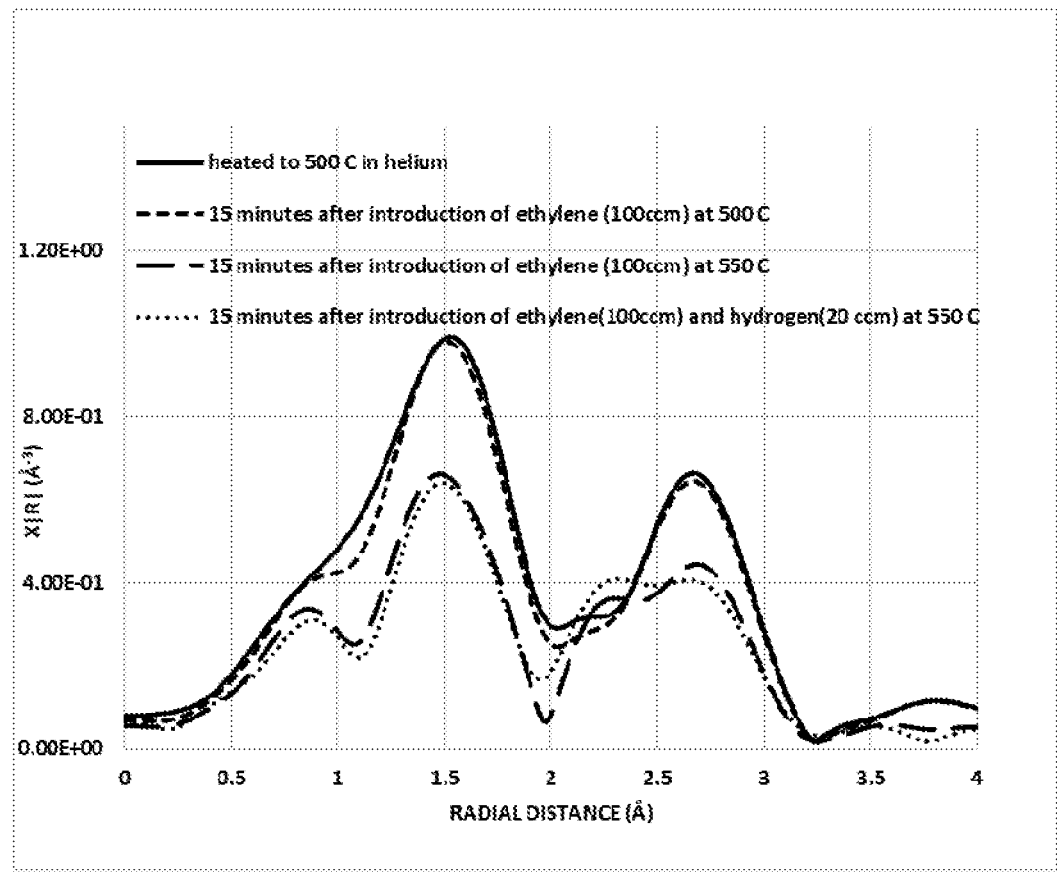
FIG. 4 shows an EXAFS spectra of the comparative Ni/$SiO_2$ catalyst provided in the Example below.

As can be seen from the Ni/SiO$_2$ EXAFS (FIG. 4), there was a decrease in peak height at ~1.5 Å that indicates the loss of Ni—O bonds. Additionally, the changes of the peak at ~2.5 Å was a sign of the formation of Ni—Ni scattering, which is direct evidence of reduction of Ni (II) to Ni (0). The EXAFS data were fit as detailed in Table III below.

TABLE III

EXAFS FITTING RESULTS

| Sample | Treatment | $S_0^2$ | C. N. | $E_0$ (eV) | R (Å) | Sigma$^2$ |
|---|---|---|---|---|---|---|
| Ni—P/SiO$_2$ | 500° C., air Measured at 500° C. 500° C., H$_2$ + C$_2$H$_4$ Measured at 500° C. 500° C., C$_2$H$_4$ Measured at 500° C. k-range: 3.0-11.0 Å$^{-1}$; R-range: 1.0-2.0 Å; R-factor: k$^1$: 0.0003; k$^2$: 0.0013; k$^3$: 0.0063 | 1.0 | 4.0 | −7.6 | 1.97 | 0.015 |
| Ni—P/SiO$_2$ | 500° C., air Measured at RT k-range: 3.0-11.0 Å$^{-1}$; R-range: 1.0-2.0 Å; R-factor: k$^1$: 0.0003; k$^2$: 0.0010; k$^3$: 0.0038 | 1.0 | 4.4 | −5.3 | 2.00 | 0.010 |
| Ni/SiO$_2$ | 500° C., air Measured at RT k-range: 3.0-11.0 Å$^{-1}$; R-range: 1.0-2.0 Å; R-factor: k$^1$: 0.0010; k$^2$: 0.0016; k$^3$: 0.0032 | 1.0 | 4.6 | −2.7 | 2.04 | 0.008 |
| Ni/SiO$_2$ | 500° C., air Measured at 500° C. k-range: 3.0-11.0 Å$^{-1}$; R-range: 1.0-2.0 Å; R-factor: k$^1$: 0.0012; k$^2$: 0.0027; k$^3$: 0.0085 | 1.0 | 4.4 | −4.7 | 2.01 | 0.013 |
| Ni/SiO$_2$ | 500° C., C$_2$H$_4$ Measured at 500° C. k-range: 3.0-11.0 Å$^{-1}$; R-range: 1.0-2.0 Å; R-factor: k$^1$: 0.0012; k$^2$: 0.0027; k$^3$: 0.0085 | 1.0 | 3.7 | −4.3 | 2.00 | 0.011 |
| Ni/SiO$_2$ | 550° C., C$_2$H$_4$ Measured at 550° C. k-range: 3.0-11.0 Å$^{-1}$; R-range: 1.0-2.0 Å; R-factor: k$^1$: 0.0012; k$^2$: 0.0027; k$^3$: 0.0085 | 1.0 | 1.8 | −5.1 | 1.97 | 0.011 |
| Ni/SiO$_2$ | 550° C., C$_2$H$_4$ + H$_2$ Measured at 550° C. k-range: 3.0-11.0 Å$^{-1}$; R-range: 1.0-2.0 Å; R-factor: k$^1$: 0.0012; k$^2$: 0.0027; k$^3$: 0.0085 | 1.0 | 1.3 | −4.7 | 1.97 | 0.002 |

From the XANES and EXAFS, the Ni—P/SiO$_2$ was stable in the presence of ethylene as well as hydrogen at higher temperature (500-550° C.) and did not show any sign of reduction to metallic Ni(0).

In case of the comparative Ni/SiO$_2$ catalyst, the shift of the EXAFS spectrum to lower energy indicated the reduction of Ni (II) to Ni (0). These changes also indicated a loss in the Ni—O coordination and increase of the Ni—Ni coordination, which is consistent with the reduction of Ni (II) ions and formation of Ni (0) nanoparticles. At 550° C., in presence of ethylene and hydrogen for fifteen minutes, the Ni (II) percentage fell to 65.9% Ni (II) (Table II), which shows the instability of Ni (II) on silica catalysts. Its coordination number also decreased from 4.6 to 1.3 (Table III) indicating a loss of tetrahedral geometry.

Based on the results and findings above, it has been surprisingly and unexpectedly discovered that Ni—OP bonds are more resistant to hydrogen reduction, and prevent Ni(II) ions from reducing at temperatures above 500° C. It was more surprising and unexpected that the Ni—P/SiO$_2$ catalyst was active at temperatures above 500° C. While the current results showed a low conversion, it is believed that increasing the pressure would increase the rate of reaction, but is unlikely to change the oxidation state of Ni(II). In contrast, the comparison catalyst Ni/SiO$_2$ did not show any ethylene oligomerization at temperatures above 500° C.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. An oligomerization catalyst, comprising:
   a nickel phosphate compound; and
   an amorphous support, wherein the nickel has a +2 oxidation state at a temperature of 500° C. or higher.

2. The catalyst of claim 1, wherein the nickel has a +2 oxidation state at a temperature of 650° C. or higher.

3. The catalyst of claim 1, wherein phosphoric acid is a source for the phosphate.

4. The catalyst of claim 1, wherein nickel nitrate hexahydrate is a source for the nickel, and the nickel is present in an amount ranging from about 2 wt % to about 20 wt %, based on the total weight of the catalyst.

5. The catalyst of claim 1, wherein the amorphous support has a surface area of about 100 $m^2/g$ to about 600 $m^2/g$.

6. The catalyst of claim 1, wherein the amorphous support has a pore size of about 50 Å to about 500 Å.

* * * * *

UNITED STATES PATENT AND TRADEMARK OFFICE
CERTIFICATE OF CORRECTION

PATENT NO. : 11,135,573 B2
APPLICATION NO. : 16/361411
DATED : October 5, 2021
INVENTOR(S) : Jeffrey T. Miller et al.

Page 1 of 1

It is certified that error appears in the above-identified patent and that said Letters Patent is hereby corrected as shown below:

In the Specification

In Column 1, Lines 5-10, the section labeled "GOVERNMENT LICENSE RIGHTS" should be removed.

Signed and Sealed this
Twelfth Day of April, 2022

Drew Hirshfeld
*Performing the Functions and Duties of the
Under Secretary of Commerce for Intellectual Property and
Director of the United States Patent and Trademark Office*